(12) United States Patent
Blake

(10) Patent No.: US 7,462,194 B1
(45) Date of Patent: Dec. 9, 2008

(54) TWO PART "L"-SHAPED PHAKIC IOL

(76) Inventor: Larry W. Blake, 31082 Vis Consuelo, Coto De Caza, CA (US) 92679

( * ) Notice: Subject to any disclaimer, the term of this patent is extended or adjusted under 35 U.S.C. 154(b) by 622 days.

(21) Appl. No.: 09/631,576

(22) Filed: Aug. 4, 2000

(51) Int. Cl.
A61F 2/16 (2006.01)

(52) U.S. Cl. .................. 623/6.46; 623/6.18; 623/6.41; 623/6.43; 623/6.47

(58) Field of Classification Search ............... 623/6.41, 623/6.46, 6.18, 6.47, 6.38, 6.43
See application file for complete search history.

(56) References Cited

U.S. PATENT DOCUMENTS

| | | | |
|---|---|---|---|
| 4,056,855 A | 11/1977 | Kelman | |
| 4,092,743 A | 6/1978 | Kelman | |
| 4,268,921 A | 5/1981 | Kelman | |
| 4,370,760 A | 2/1983 | Kelman | |
| 4,434,515 A * | 3/1984 | Poler | 623/6.41 |
| 4,608,049 A | 8/1986 | Kelman | |
| 4,636,210 A | 1/1987 | Hoffer | |
| 4,725,276 A * | 2/1988 | Bissonette et al. | 623/6.15 |
| 4,769,035 A | 9/1988 | Kelman | |
| 4,781,718 A * | 11/1988 | Lindstrom | 623/6.46 |
| 4,911,715 A | 3/1990 | Kelman | |
| 5,074,876 A | 12/1991 | Kelman | |
| 5,141,507 A * | 8/1992 | Parekh | 623/6.41 |
| 5,201,763 A * | 4/1993 | Brady et al. | 623/6.41 |
| 5,222,981 A * | 6/1993 | Werblin | 623/6.34 |
| 5,306,297 A * | 4/1994 | Rheinish et al. | 623/6.38 |
| 5,366,502 A | 11/1994 | Patel | |
| 5,769,889 A | 6/1998 | Kelman | |
| 6,413,277 B1 * | 7/2002 | Neuhann | 623/6.39 |
| 6,425,917 B1 * | 7/2002 | Blake | 623/6.42 |
| 2002/0022882 A1 * | 2/2002 | Morgan et al. | 623/6.18 |
| 2002/0045938 A1 * | 4/2002 | Brady et al. | 623/6.18 |
| 2003/0045933 A1 * | 3/2003 | Brady | 623/6.46 |

FOREIGN PATENT DOCUMENTS

| | | | |
|---|---|---|---|
| DE | 3626869 A1 * | 2/1988 | |
| DE | 92 08 015.4 | 9/1992 | |
| EP | 1 138 282 A1 * | 4/2001 | |
| FR | 2 728 459 A1 * | 6/1996 | |
| FR | 2770394 A1 * | 5/1999 | |
| FR | 2 782 912 A | 3/2000 | |
| FR | 2 784 575 A | 4/2000 | |
| GB | 2 171 912 A | 9/1986 | |
| WO | WO 94/05233 A1 * | 3/1994 | |
| WO | WO 02/060346 A2 * | 8/2002 | |

OTHER PUBLICATIONS

English translation for FR 2,728,459.*

* cited by examiner

Primary Examiner—David H. Willse
Assistant Examiner—Javier G Blanco
(74) Attorney, Agent, or Firm—William L. Klima; Klima Law Office, PLLC

(57) ABSTRACT

A multi-part IOL which is insertable through an opening as small as about 1 mm without deforming the haptic, is described. This IOL may be used in the anterior chamber of the eye for phakic or aphakic lenses. After insertion of the haptic into the eye, any type of lens may be attached, especially by use of cleats. The haptic is a high modulus skeletal frame, and may be assembled with lower modulus material. An eyelet may be provided on the lens allowing a cleat on the haptic to firmly attach to the optic.

29 Claims, 13 Drawing Sheets

TWO PART "L"-SHAPED PHAKIC IOL

FIELD OF THE INVENTION

The present invention generally relates to a two part "L"-shaped IOL. More specifically, the present invention relates to an IOL film frame which is insertable through an opening as small as 1.0 mm without deforming the frame and a lens which can then be attached within the eye.

BACKGROUND OF THE INVENTION

The history of intraocular lenses (IOLs) is a long and varied one. Intraocular lenses can be used to treat a wide diversity of eye conditions ranging from cataracts to any type of eyesight correction. In addition, IOLs can be used to replace an irreversibly damaged lens in the eye—aphakic eyes. Alternatively, the lenses can be used in addition to the natural lens to correct the vision—phakic eyes. These lenses can be placed in the anterior or posterior chambers of the eye.

Early IOL researchers were plagued with problems associated with the materials which were obtainable to them at the time (early 1950's) making the lenses too heavy and too large. Surgery of the eye was in its infancy and therefore there were many problems with the surgical procedures. Since that time the quality, size and weight of the optics as well as microsurgical procedures have dramatically improved.

The earliest IOL's were placed in the anterior chamber of the eye, this being the easiest chamber to get to. Along with the early problems with the optics and surgical techniques, placement of a lens in the anterior chamber proved difficult because the anterior chamber is narrow (about 1.5 to 2.5 mm).

The second location is the angle between the cornea and the iris. Angle supported anterior chamber IOLs took advantage of the anterior chamber angle to support and fix the IOL in place. By angling the IOL into opposite sides of the anterior chamber, the natural angle was used to keep the IOL from moving. However, early lenses experienced marked problems with endothelial loss due to chafing against the early thick lenses. Later lenses were able to reduce the significance of this problem, but still retained problems associated with placement of the IOL in the chamber angle. The biological properties of that angle make it a very sensitive area. The structures associated with equalizing the internal pressure of the eye are located in that area. Additionally, the tissue in the area is easily irritated and irritation initiates a growth of fibrous tissue, called synechiae. The IOL fixation must be gentle in order to reduce irritation, but stable enough that it will not be easily moveable. This compromise is difficult to obtain. In addition, although the results were excellent in the short-term, there was a significant problem in the long term with altered night vision, loss of endothelial cell populations and alteration of the anterior uvea. These problems as well as the fact that such anteriorly positioned lenses were uncomfortable to the patient, caused many doctors to abandon anterior chamber IOL's.

A third location was developed later and involves implanting a contact lens between the iris and the natural lens. These lenses are called ICL's or implantable contact lenses. However, the ICL's are suspected of initiating cataracts and glaucoma.

As the development of the IOL's became more sophisticated, Ophthalmologists recognized various problems. A typical IOL is composed of an optic, the 'lens' part of the structure, and a mounting mechanism called a haptic. The haptics are the part of the IOL that comes in contact with the eye tissue to hold the lens optic in place. There were essentially two major types of haptics which were developed—fiber and plate haptics. Fiber haptics are slender strands of resilient material which are attached at one end to the optic, and which rest, at their other end, against the eye. Fiber haptics have the advantage of being very light and slender. This would seem to make them ideal by causing less damage to the tissue and additionally being aesthetically pleasing because they are very narrow. The slenderness makes it more difficult for someone looking at the patient to see the IOL through the eye. Plate haptics are machined or molded from stock materials and have a central optic and an outer perimeter which rests against the eye. Because of their size, plate haptics tend to be more easily seen from outside in the patient's eye and the addition of extra material weight to the IOL and reduced flexibility as compared to fiber haptics leads to poor fixation and consequent migration or dislocation of the IOL. While, fiber haptics have the disadvantage of initiating a process in which the body builds fibrous tissue or synechiae around the fiber haptic which immobilizes the iris, the larger plate haptic very rarely, if ever, causes such a reaction.

The adverse problems associated with the earlier anterior chamber haptic designs encouraged the development of IOL's for the posterior chamber for the majority of implants.

The surgical process may or may not include removal of the diseased natural lens using a process called phakoemulsification. The more standardized procedure for lens implantation involves removal of a diseased natural lens followed by implantation of an artificial lens. Phakoemulsification of the diseased lens is accomplished through about a 2 to 4 mm (small) incision in the eye and through a capsulorhexis incision in the capsule that encloses the lens in the posterior chamber, then an artificial intraocular lens implant is implanted back through the capsulorhexis into the capsular bag. For other types of procedures, the natural lens may not require removal at all.

As surgical procedures have developed, there is a trend toward reducing the size of the incision in the eye. Although a 3 mm incision does not usually require sutures for healing, it increases the chances of infection, heals slower, and may provide for a slower operation then if an incision of less than 3 mm is used. However, presently IOLs cannot be inserted into a very small incision, as small as 1 mm.

SUMMARY OF THE INVENTION

Accordingly, an intraocular lens (IOL) has been developed. The intraocular lens features an optic and a haptic. The haptic is "V"-shaped and features relatively more rigid elements formed of relatively higher modulus (harder) materials which are flexibly springy when thin. The haptics may also comprise less rigid elements formed of relatively lower modulus (softer) materials bridging a discontinuity separating the haptics. The "V"-shaped haptic allows for insertion of the haptic through an opening in the eye as small as about 1 mm without deforming the frame. The haptic also features a fastening structure for the separate optic, preferably a cleat. The foldable optic is then inserted into the eye through the same ultra small incision and attached to the haptic, preferably the haptic cleat, by way of a formed aperture or eyelet in the optic.

The higher modulus springy polymeric material may be selected from polyimide, polyetheretherketone, polycarbonate, polymethylpentene, polymethylmethyl methacrylate, polypropylene, polyvinylidene fluoride, polysulfone, and polyether sulfone. Preferably, the higher modulus material is polyphenylsulfone (PPSU). Preferably, the higher modulus material has a modulus of elasticity of about 100,000 to about 500,000 psi, even more preferably about 340,000 psi and has a hardness of about 60 to 95 on the shore D scale, but more specifically a Rockwell R hardness of 120 to 130. The lower modulus rubbery material may be an elastomer selected from silicones, urethane, or hydrophilic acrylics. Preferably, the lower modulus elastomeric material has a modulus of about 100 to about 1000 psi (unit load at 300% elongation). Preferably, lower modulus material has a hardness of about 15 to 70 on the shore A scale of hardness. Preferably, the lower modulus material is a dispersion such as NUSIL MED 6605, 6400, 6820, 6604, and 6607, or the like.

In one embodiment, the relatively more rigid elements comprises a "V"-shaped frame. The frame forms three haptics which may be formed from a single uniform piece of material. The haptic may contain a cleat for attachment of the lens. The haptic may additionally contain a slot open on one side to form a hinge which is bendable at the slot. The haptic may alternatively contain a groove to form a hinge which is bendable at the groove.

The lower modulus material may partially or completely cover the haptics. In one embodiment, the lower modulus material is extended beyond the tip of the haptic to produce a softer contact point for the eye tissue. The lower modulus material may be applied by first surface treating the higher modulus material and then molding the lower modulus material onto the treated surface. Preferably, the surface treatment is a corona or plasma treatment and additionally a primer. Preferably, the molding is dip molding, cast molding, or injection molding. Primers such as Nusil Med may also be used singly or in combination.

The invention is a "V"-shaped intraocular lens frame, having multiple plate haptic elements preferably formed of relatively higher modulus harder material and containing an attachment for a separate optic.

The invention may optionally have a hinge connecting the toe region to the foot region, the hinge being formed of relatively lower modulus material. This can be referred to as a "duplex" material.

The optic may be any type of lens. Preferably, the optic is a refractive lens, or an interference lens, producing a thin optic. The optic could be toric, aspheric, multi-element, positive or negative.

Further, the invention is an intraocular lens having an optic; and a haptic including stiffer elements joined by flexible elements of different materials.

Still further, the invention is a method for making an intraocular lens haptic, having the steps of forming a frame, coating a location of the frame, and breaking the frame at the location.

Still further, the invention is a method of mounting a lens in the anterior chamber of an eye, having the steps of supporting a lens on a plate haptic at the angle of the anterior chamber; and bending the haptic at a preferential hinge line to reduce pressure against the angle.

DETAILED DESCRIPTION OF THE PREFERRED EMBODIMENT

Accordingly, a haptic in the form of a "V"-shape has been developed for a two part IOL. This thin film frame haptic is insertable through an opening in the eye as small as about 1 mm without deformation of the haptic. This film frame haptic is also lightweight, springy and non-irritating, low cost, surgically implantable with a minimum of trauma to the eye, aesthetically pleasing, and does not support fibrous tissue growth. This IOL works in the anterior or posterior chamber of the eye for phakic or aphakic lenses. This haptic additionally comprises a fastener for a separate optic.

This "V"-shaped IOL film frame is a haptic system based on a high modulus, shaped skeletal frame or plate haptic. The haptic system may optionally be assembled with low modulus, soft, elastomeric hinged zones. The more rigid frame or haptic in combination with the soft hinges ensures that the lens and haptic assembly will maintain its shape and stay ideally situated in the anterior chamber angle of the eye or in the posterior chamber. Whereas, a haptic of a single soft material will not maintain a desirable shape and will be more noodle-like in its spirit, the compliant hinge can automatically adjust to the normal movements of an eye.

Figure 1:
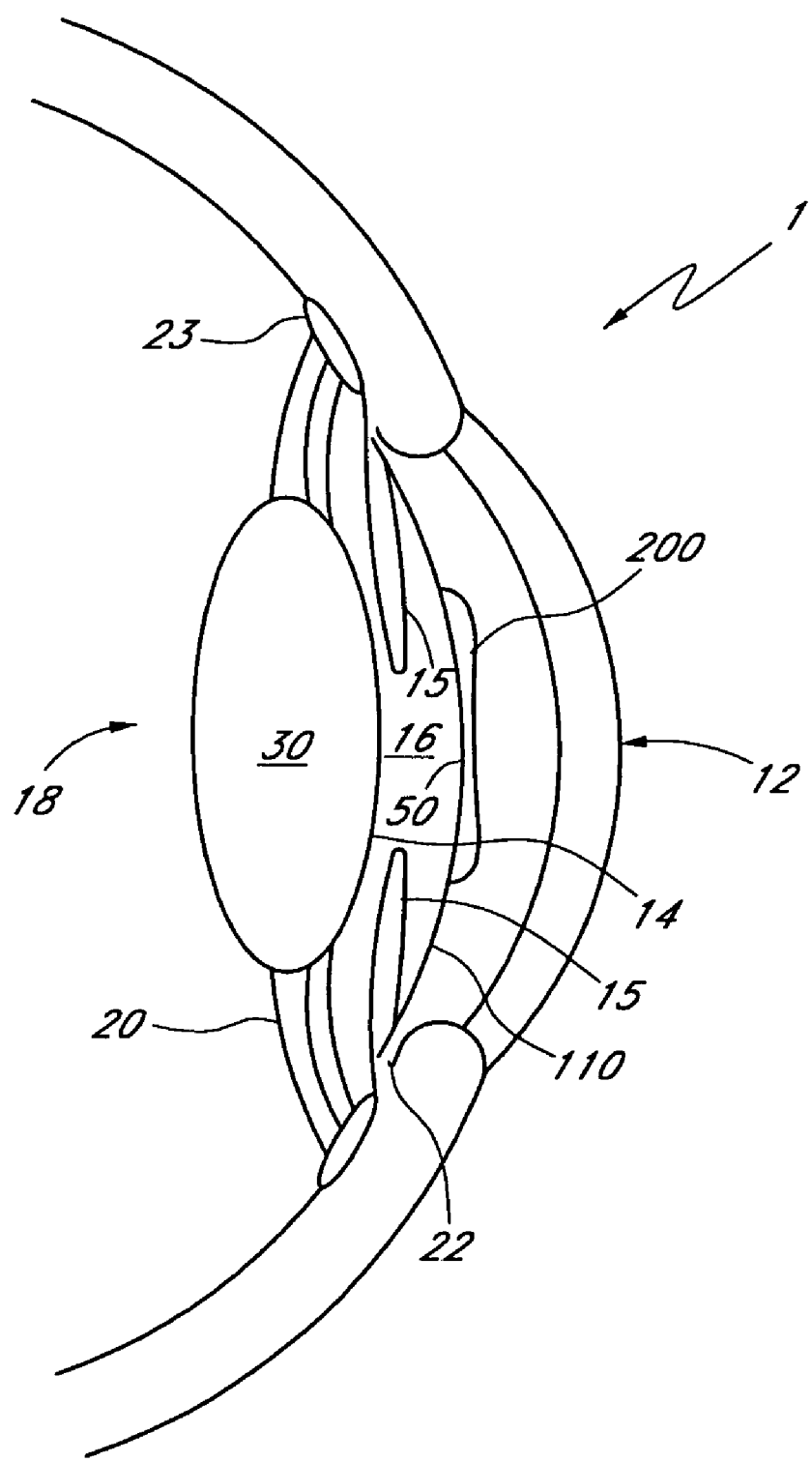
FIG. 1 is a simplified representation of the cross-sectional physiology of the eye with an anterior IOL in accordance with the preferred embodiment implanted.

Referring to FIG. 1, the cornea 12 serves as a refracting medium in addition to its function as the anterior wall of the eye 1. The pupil 14 and the iris 15 of variable aperture are located behind the cornea 12 and divide the eye 1 into an anterior chamber 16 and a posterior chamber 18. The natural crystalline lens 30 is connected by zonular fibers to a peripheral muscle about the lens 30 known as the ciliary muscle 20.

The more standardized procedure for the removal of a diseased natural lens 30 followed by implantation of an artificial lens involves the phakoemulsification of the diseased lens through a small incision in the eye and through a capsulorhexis incision in the capsule that encloses the lens in the posterior chamber 18, then an artificial intraocular lens implant is implanted back through the capsulorhexus into the capsular bag. For other types of procedures, the natural lens 30 may not require removal at all. The optic 200 of the IOL 10 used in these procedures includes a separate centrally located optical zone and may be configured for implantation into either the anterior 16 or posterior chamber 18 and may be used for either procedure set out above. The haptic 110 of the IOL 10 extends radially outwardly in the general plane of the optic 200.

Figure 2A:
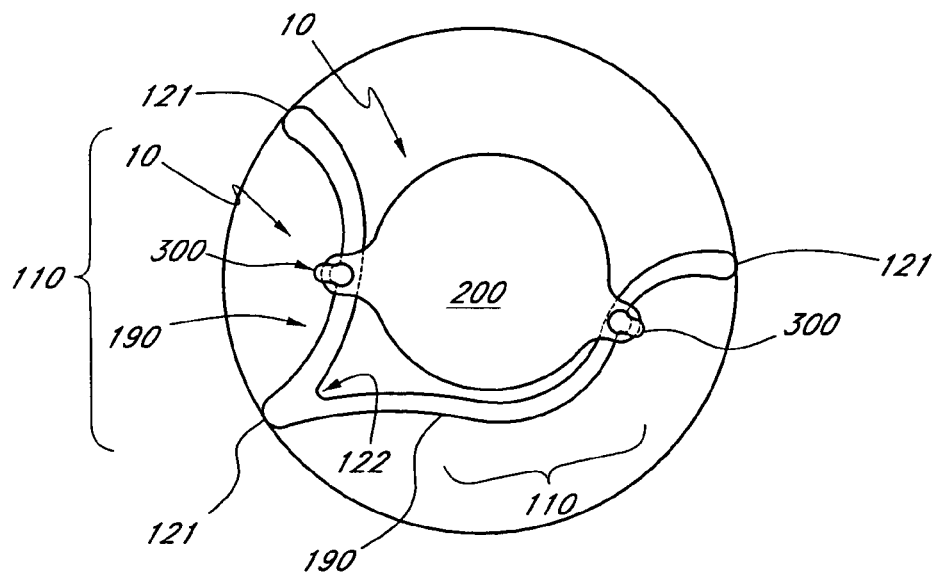
FIG. 2A is a plan view of the multi-part IOL in accordance with the preferred embodiment within the eye.
Figure 2B:
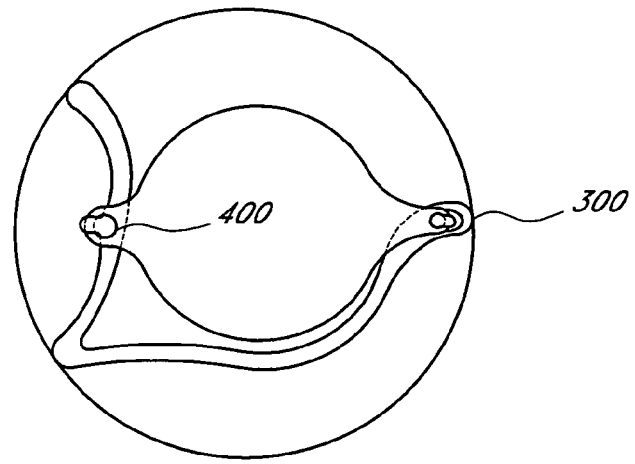
FIG. 2B is a plan view of an alternate embodiment of the positioning of the cleat in accordance with the preferred embodiment.
Figure 2C:
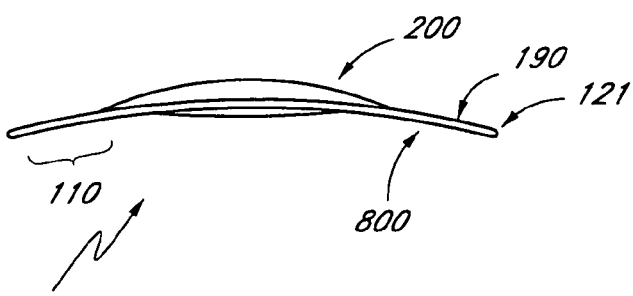
FIG. 2C is a side view of the multi-part IOL in accordance with the preferred embodiment.
Figure 3:
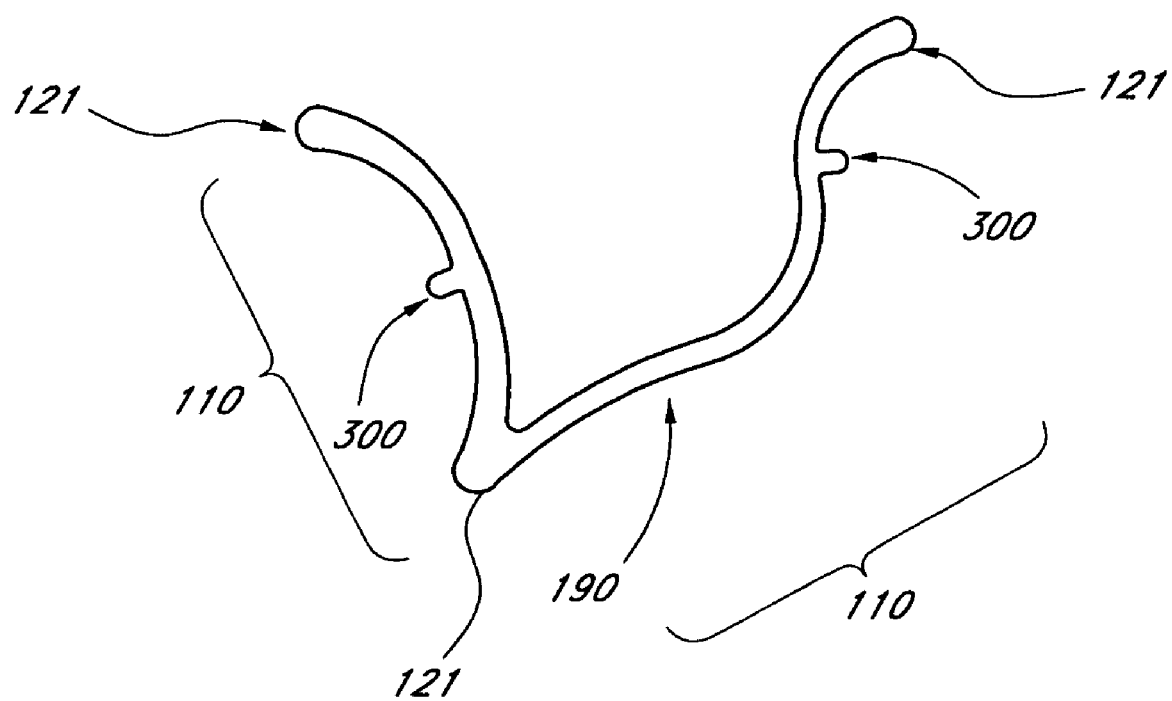
FIG. 3 is a plan view of the haptic in accordance with the preferred embodiment.

With reference now to FIGS. 2 and 3, the multi-part IOL arranged and configured in accordance with certain features, aspects and advantages of the present invention will be described in detail. FIGS. 2 and 3 are plan views of the film frame haptic of a plural part IOL 10 in accordance with the preferred embodiment. The intraocular lens 10 is generally comprised of a lens optic 200 and a lens frame haptic 110. The film frame haptic 110 includes three feet 121 and two cross bars 190. The three feet 121 and two cross bars 121 are arranged in an approximately "L"-shape. By "L" shape, it is envisioned that there is at least one "corner" or "angle" 122 which is as great as 135° or more, but preferably at about a 90° angle or less, preferably between 35 and 60° (angular degrees) and more preferably about 45°. This arrangement allows the haptic to be inserted into a very small incision without deformation of the haptic. The very small incision is preferably less than 3 mm, more preferably less than 2 mm, and even more preferably less than 1.5 mm and most preferably less than about 1.0 mm. The maximum dimension across the width of the haptic 110, at all points, is less than the incision. It is understood that, due to the fact that living tissue is very elastic and will yield a little, the incision in the eye can be stretched without damage to the tissue. For example, it has been observed that a 2.5 mm incision can be stretched to as much as 3 mm, to allow passage of a 3 mm wide haptic arm.

In a preferred embodiment, each foot 121 may have a hinge region 120 which can be configured in a number of ways, but has the property of being more elastic than the main body of the foot 121. This hinge region 120 is formed of a material which is more elastic than the remainder of the lens frame haptic 110. In the preferred embodiment, the hinge region 120 is covered in an elastomeric material 127 which extends between the foot 121 and toe 150. The hinge zone 120 can be a thinner section in the frame, or a discontinuous opening in the frame where the elastomer 127 extends between the foot zone 121 and the toe portion 150. The hinge 120 and toe 150 can be produced in a variety of ways which are described in detail in application Ser. No. 09/570,301, filed May 12, 2000.

With further reference to FIGS. 2B and 3, the separate lens optic 200 can be any type of lens, elastomeric or polymeric optical material. The optic 200 can be a simple refractive lens, a monofocal, toric or aspheric, a bifocal, an interference lens, a positive lens or a negative lens. The lens can be made thinner by using the polychromatic diffractive lens disclosed in U.S. Pat. No. 5,589,982 which is hereby incorporated herein by reference. Optionally a regular lens can be made thinner by edge-bonding, or bonding the haptic to the outside of the lens as disclosed herein rather then burrowing a hole into the side of the lens as is done routinely. The lens optic 200 can be made of silicone (Optical index N=1.40 to 1.46), soft acrylic (N=1.40 to 1.46), hydrophilic acrylic, or methyl methacrylate (N=1.49) or polyphenylsulfone (N=1.67). Alternatively, the lens optic 200 may be made of the same material as the film frame haptic 110 and can be made of a material as low as 15 shore on the A scale.

The lens optic 200 can be attached to the frame haptic 110 in a variety of ways. A preferred embodiment is shown in FIG. 2B, in which the optic includes eyelets 400 which permit attachment of the lens to the cleats 300 on the haptic.

Figure 4A:
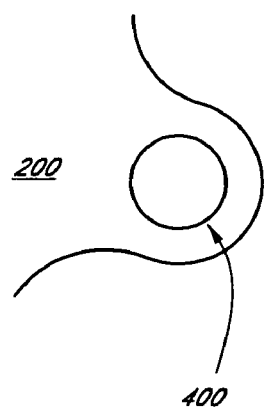
FIGS. 4A-C are plan and side views of the cleat and eyelet used to attach the ocular onto the haptic.
Figure 4B:
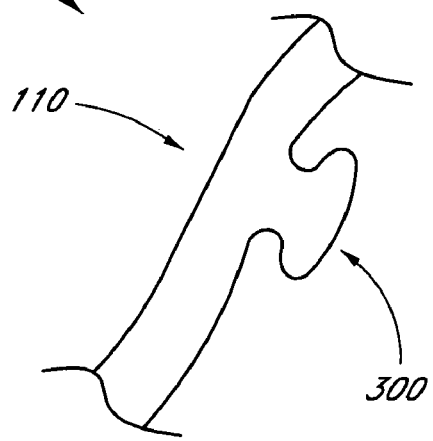
Figure 4C:
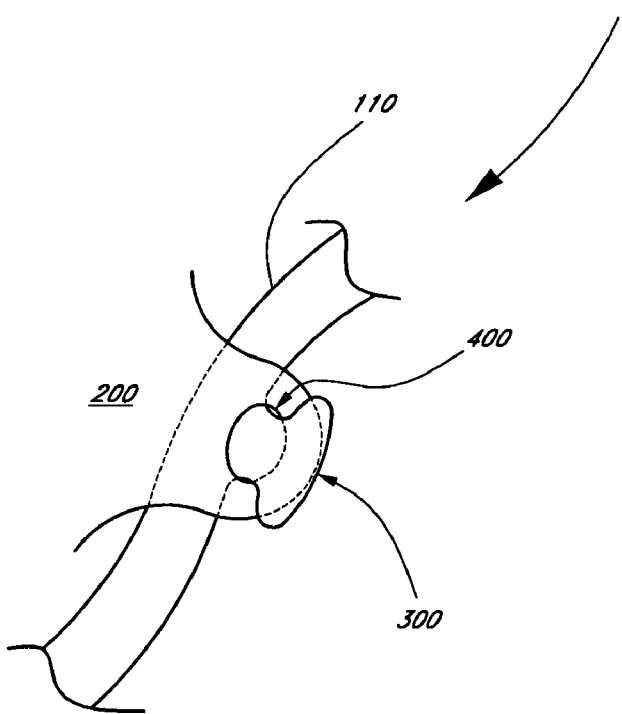

In one embodiment, shown in FIG. 4, the cleat 300 is shaped in such a way that the eyelet 400 will not easily be detached. It is envisioned that the surgeon can attach the optic 200 to the haptic within the eye using a forceps. The haptic 110 is inserted into the very small opening and positioned in the eye as desired (see FIG. 5A-E). Then the optic 200 is rolled or folded as needed and inserted into the eye with forceps and attached to the furthest cleat 300 from the opening (FIGS. 5F and G). As the forceps are removed, the eyelet 400 on the other side of the optic 200 can be attached to the cleat 300 closest to the opening (FIG. 5H). In a preferred embodiment, the optic 200 is produced of a material with a lower modulus then the haptic 110, thus allowing the eyelet to be slightly stretched as the haptic is slightly sprung to allow a stronger attachment of the optic eyelets 400 to the cleats 300 on the haptic 110. In one embodiment it is envisioned that one side of the optic 200 can be fastened before insertion of the IOL 10 into the eye. The optics of this invention can be made with very thin edges (as thin or as low as 10µ) to help reduce edge glare.

With reference to FIGS. 2A-2C it can be seen that the cleats 300 extend generally in the plane of the haptic 110. With specific reference to FIG. 2A it can be seen that the cleats 300 may be arranged such that they are not diametrically opposed. An advantage of this is that lenses can be used which are not symmetrical, allowing for treatment of astigmatism. For example if a lens needs to be inserted and positioned in a specific orientation, it can be more easily done with this asymmetry as a visual aid. In addition, multifocal optics can be used which allow for correction of a variety of eyesight imperfections. The addition of a third cleat 300 would allow control of asymmetric as well as symetric features.

The cleats 300 of the invention have been shown to work particularly well for the intended purpose. Therefore it is envisioned that they could be used to attach any type of IOL before insertion or after insertion. In addition, they would allow the surgeon a choice of lenses or powers to insert and the surgeon could potentially clip one or more lenses onto the cleat 300. A further aid to the surgeon would be to tint the cleats 300 and/or eyelets 400 such that they would be more visually identifiable to the surgeon during the operation.

With reference to FIG. 2B, the film frame haptics 110 and feet 121 are preferably manufactured from a high modulus material. High modulus materials are generally relatively stiff, or hard, but springy and permit relatively little elongation before they break. Such materials are often brittle and have a high permanent set, but retain their shape after formation. Preferably, the high modulus material is a biocompatible thermoplastic film such as polyimide, polyetheretherketone, polycarbonate, polymethylpentene, polymethylmethyl methacrylate, polypropylene, polyvinylidene fluoride, polysulfone, and polyether or polyphenyl sulfone. These are often referred to as "engineering plastics". They have high tensile strength and are biocompatible, hydrolytically stable, and autoclavable for sterility, and have a high modulus ranging from a tensile modulus of about 100,000 to 500,000 psi (using test method D 638 of the ASTM). The material can be clear, opaque, or tinted, but is preferably clear. However, in many cases, even a tinted material, if produced thinly enough, will appear clear in the eye. The frame 110 and feet 121 may be cut from a sheet by machining, stamping, chemical machining, water jet machining or photomachining with an excimer or YAG laser. The sheet material may also be punch stamped, perforated, photochemically or photo-optically shaped. An alternative method for production of the film frame 110 includes molding the high modulus material into the desired shape. It is generally known in the plastics art to identify thin sheets of plastics less than 0.010 inches thick as "films", that definition is used herein. The eyelet aperture hole is about 0.1 mm to 1.2 mm, preferably 0.5 mm. The thickness can be 0.001 to 0.010 inches, preferably 0.002 to 0.003 inches.

After photo-cutting, the arcuate vaulting curves and shapes are secondarily formed into the haptic by mounting the frame on a dihedral shaped tool or equivalent and baked in an oven between 150° F. up to 550° F. depending on the haptic machine requirements.

The film frame haptic 110 is typically next polished to remove any rough edges. The preferred method of polishing involves abrasive tumble agitation polishing with glass beads. An alternative method for polishing the film frame haptic 110 and feet 121 includes flame polishing. At least the areas of the film frame or haptic 110 away from the optic region, which are to be hinges, are then treated such that an elastomeric compound can be attached. An alternative surface treatment includes plasma (a low pressure corona treatment) treating. Alternatively, the entire frame 110 could be surface treated or primed. Additionally, surface roughening such as by grit or vapor blasting can be included.

In the preferred embodiment, the frame haptic 110 is polyphenylsulfone which has a tensile modulus of about 340,000 psi (using test method D 638 of the ASTM) and is clear but exhibits a natural UV light absorbence property below 400 nm's resulting in a yellowish or amber tint. The frame haptic 110 is preferably made from film which is generally ≦0.025 cm (0.010 inches) thick, preferably 0.001 to 0.005 inches thick, but could be as thick as 0.012 inches or even as thin as 0.0005 inches. In the preferred embodiment the feet 121 are identical, but, non-identical feet 121 configurations can be paired for use in an alternative embodiment when necessary. The thinness of the film frame haptic 110 contributes to its springiness and lightness which is advantageous in that the IOL is less likely to be disrupted from its initial position.

The film lenses of these designs are typically about half the weight of a standard lens and can be between 2 to 10 milligrams and as low as 1 milligram in weight in air and about 10% of this when in the aqueous of the eye. Preferably the lens is flexible but may be made of a hard, stiff, low memory material. However, in the preferred embodiment, the lens is made of silicone and the chosen silicone can be as low as 15 shore A. The index (N) value would be 1.430 to 1.460.

Figure 5A:
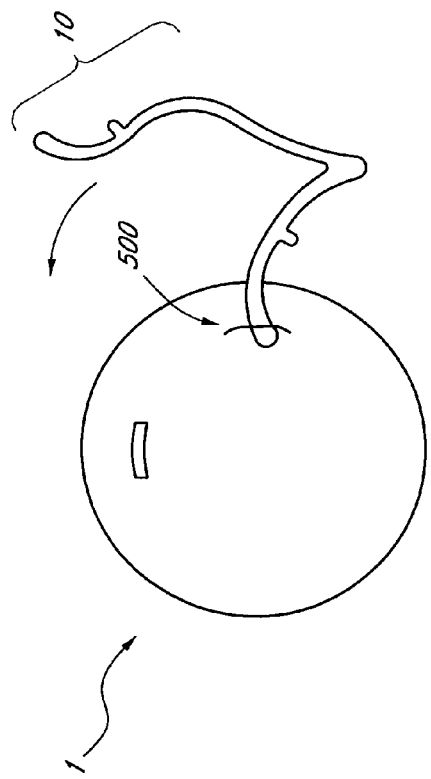
FIGS. 5A-H is a plan view of the haptic and lens being inserted into an eye through an ultra-small incision. The arrows indicate which way the haptic is moved to allow insertion without deformation.
Figure 5B:
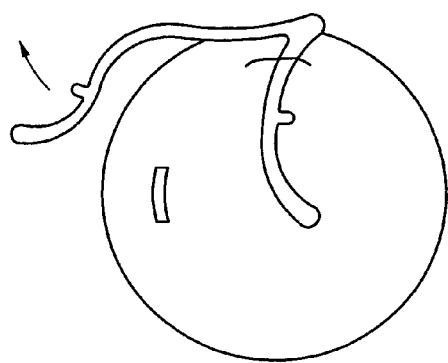
Figure 5E:
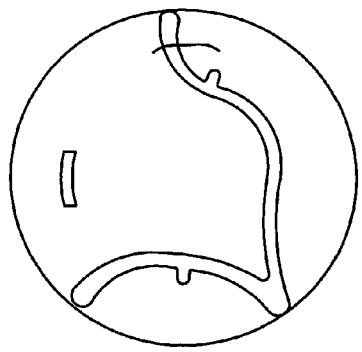
Figure 5D:
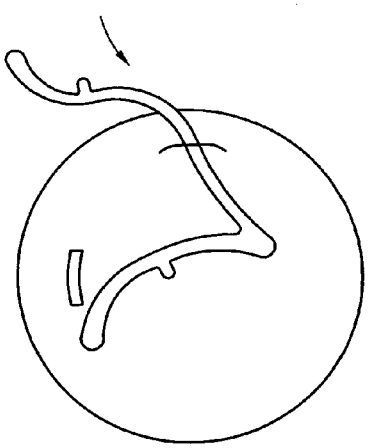
Figure 5C:
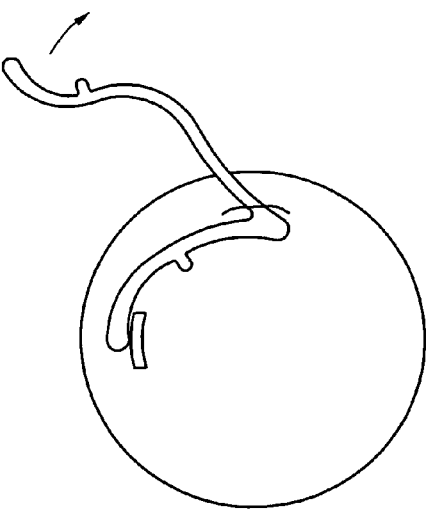
Figure 5F:
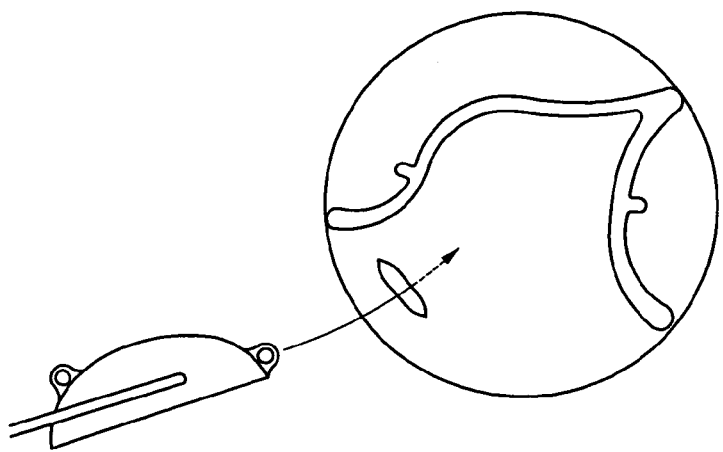
Figure 5G:
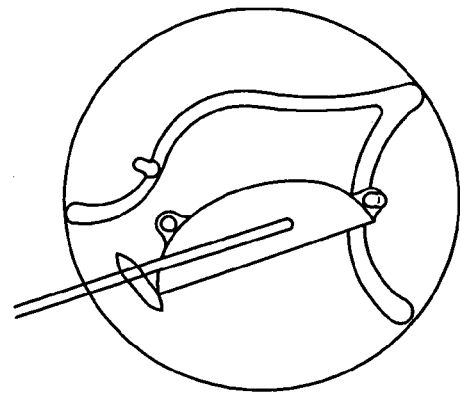
Figure 5H:
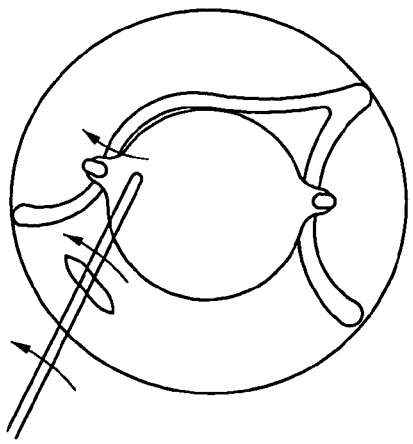
Figure 6A:
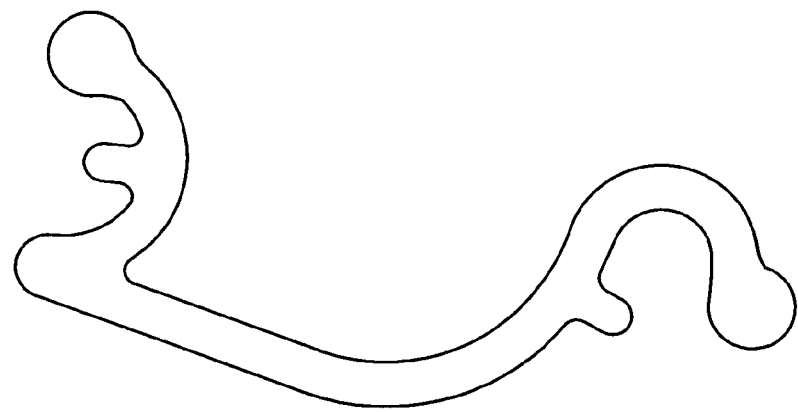
FIGS. 6A-C are plan views of alternative "L" shapes for the haptic of the invention.
Figure 6B:
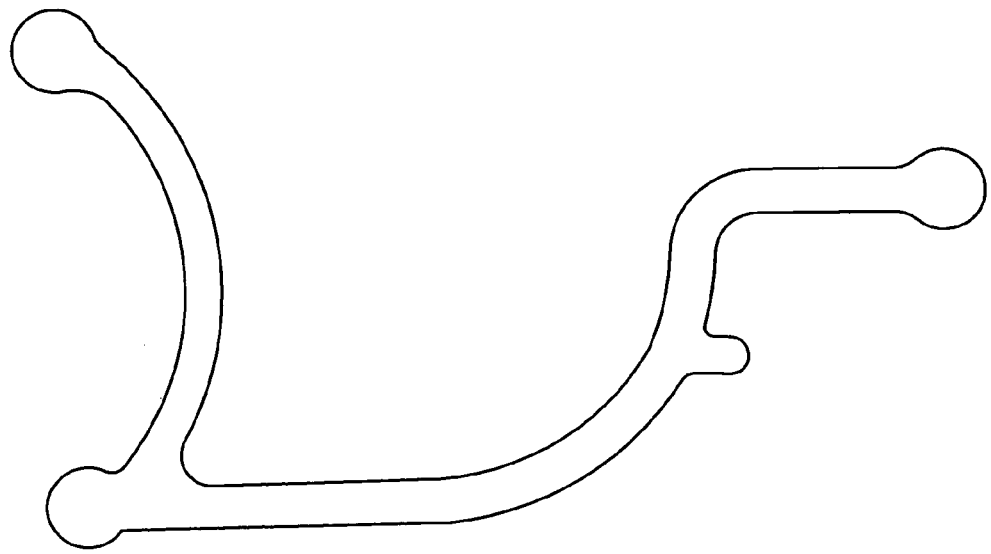
Figure 6C:
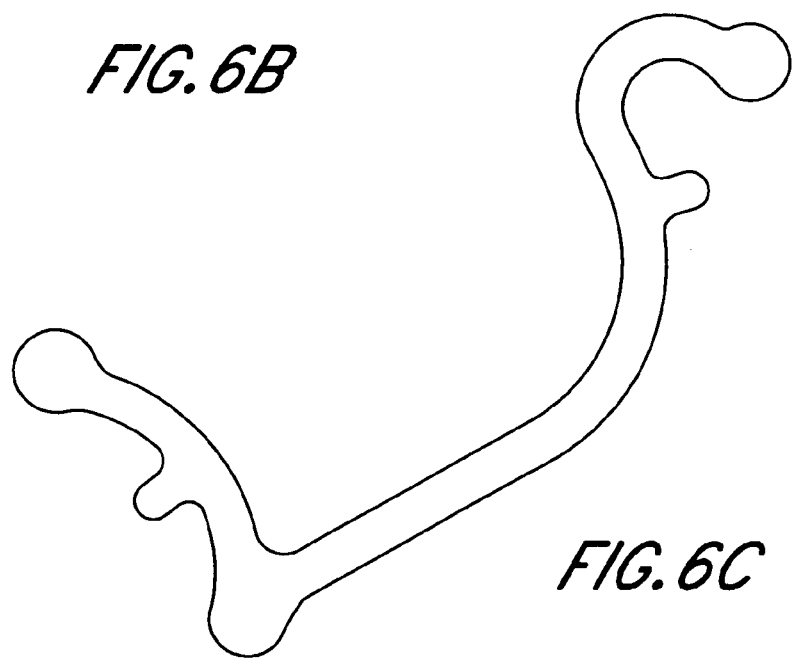

FIGS. 5A-E illustrate how the haptic can be manipulated through a very small incision without deformation. This is preferable to a haptic which may posses a hinge or be "foldable" because it requires no lateral movement or unfolding within the very narrow confines of the posterior chamber of the eye and which may contribute to damage within the eye. In FIGS. 5A-E, the "L"-shaped haptic allows for insertion through a very small incision 500 by rotating the haptic as it is manipulated and moved into the eye 1. The dimensions of the haptic are such that the greatest cross-sectional dimension at any point along the haptic is less than 2 mm. FIG. 5A shows the haptic initially being inserted into the incision starting at the short arm of the "L" up to the "corner" 122. At this point (FIG. 5B) the haptic is manipulated such that the "corner" is inserted and the haptic is rotated (5C) until the short arm of the haptic lines up with the edge of the eye and the long arm is about perpendicular to the incision. The long arm is inserted by pushing the haptic straight in (5D). Because of the position of the incision in the eye, the last step (FIG. 5F) may require a slight axial shortening of the haptic by slightly springing it inwardly to be fully inserted into the eye 1. Such springing is distinguished from the distortions, such as folding bending or rolling, normally used to introduce an intraocular lens into the eye. It can be envisioned that a number of different "L" shapes could be used to produce such a haptic. FIGS. 6A-C shows three other examples of the "L" shape.

After the haptic 110 is inserted into the very small opening and positioned in the eye as desired (see FIGS. 5A-E), the optic 200 is rolled or folded as needed and inserted into the eye with forceps and attached to the furthest cleat 300 from the opening (FIGS. 5F and G). As the forceps are removed, the eyelet 400 on the other side of the optic 200 can be attached to the cleat 300 closest to the opening (FIG. 5H).

Figure 7:
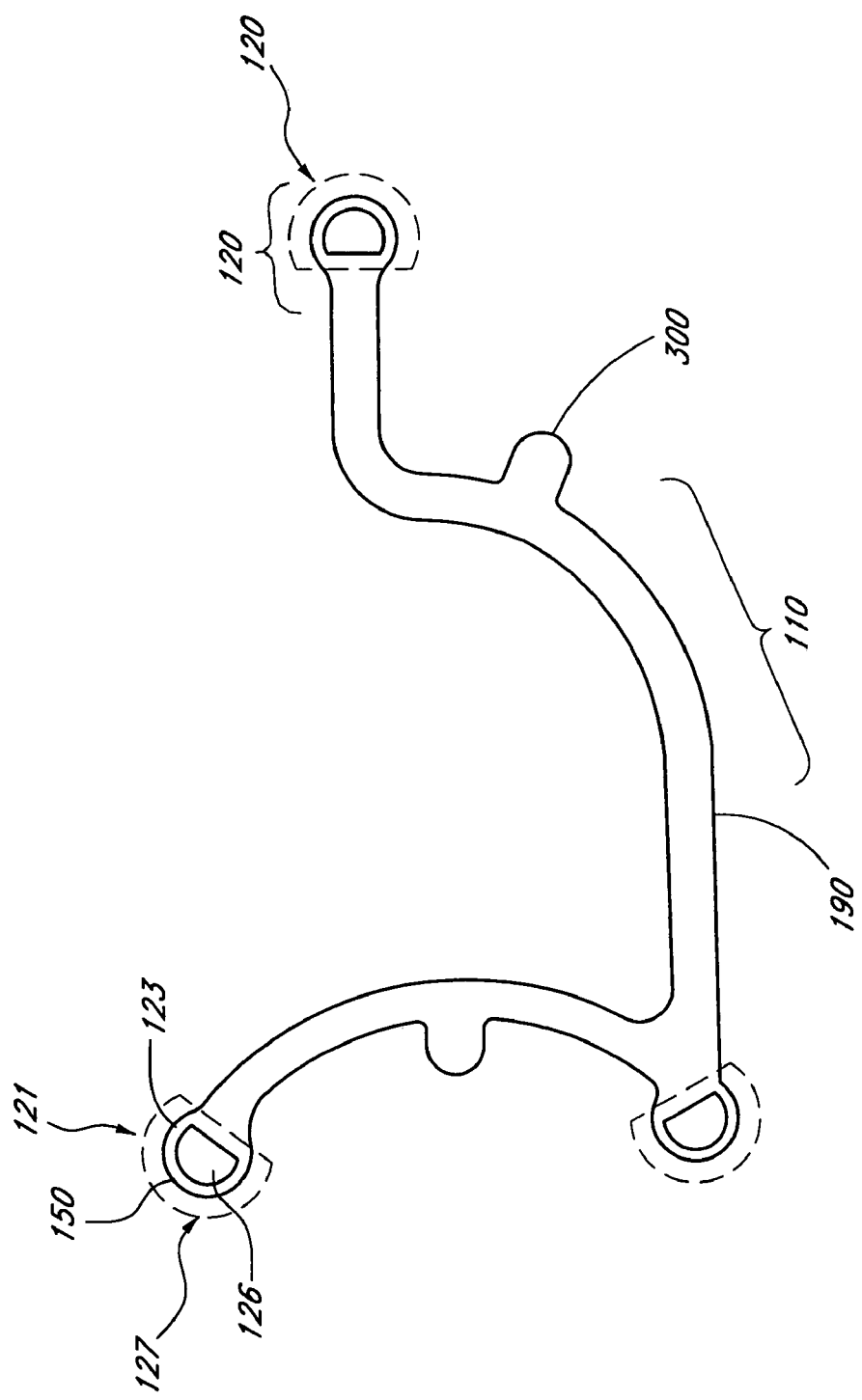
FIG. 7 is a plan view of a preferred embodiment of the haptic containing hinged feet.

With reference to FIG. 7, the film frame/haptic 110 comprises three areas which come in contact with the eye tissue. The feet 121 and toes 150 function like plate haptics and, as such, differ from the fiber haptics of the prior art. The hinged "toe" 150 is attached to the foot so that will easily pivot to adjust into a better fit while maintaining lens centration.

With continued reference to FIG. 7, the feet 121 include a hinge region 120. The hinge region 120 permits each toe 150 to have a relaxed position which can be at a slight angle to the plane of the film frame 110 and the rest of the foot 121. This slight angle permits each foot 121 to fit into the posterior chamber in such a way that the IOL 10 will be gently secured using the low mechanical loads produced by the flexible hinge region 120 combined with the flexible frame. The flexible frame can additionally be arcuately curved or shaped with a dihedral angle to more closely approximate the eye shape. More specifically, the toe region 150 is preferably made up of a loop 126 (see FIG. 2B), such that one end of the loop 126, or slotted region, is spaced from the foot 121 to form an opening 122. The other end of the loop 126 is attached to the foot 121 by a notched or thinned region 123, which temporarily supports the loop 126 in place during fabrication.

With reference to FIG. 7, the hinge regions 120 are treated in such a way that a lower modulus material can be coated onto the higher modulus material completely, or partially to connect the toe 150 and foot 121 regions as explained above. The coating for the hinge 120 and toe 150 is made from an elastomeric material which has a lower modulus (rubbery) than that of the harder film frame haptic 110. A low modulus or softer material has high elongation and high memory to urge the toe back into its original position when compressed and is preferably snappy like laytex surgeons gloves. The more rigid frame haptic 110 provides the conforming shape while the elastamer provides a resilient hinge 120, similar to a person's feet and toes. A rubbery hinge connecting rigid frame members functions, such that, when bent, the outer rubbery surface is tensioned and the inner rubbery surface is compressed. A variety of biocompatable elastomers such as urethanes and silicone dispersions such as NUSIL MED 6605, 6400, or 6820 can be used as elastomers for the hinge 120 covering. The high modulus material can be surface treated using corona, plasma, or primers, individually or in combination. Next a primer is applied and lastly, the elastomer or low modulus material can be added by dipping at least each foot 121 into the coating and subsequently curing it. The low modulus material is mechanically attached or chemically attached, and may be applied by cast molding as well as injection molding. In the preferred embodiment the process can be repeated. For example, the hinge region 120 and foot region 121 are dip coated multiple times with a dispersion, dispersions contain solvents that evaporate leaving behind thinner coatings so that the thickness would be less than is would be if the dispersion were not in a solvent. However, alternative embodiments do not require multiple dipping. A protocol for the coating process is included in Example 1.

After coating, the hinge regions 120 may be produced by breaking the high modulus material at the hinges 120, scores, or notches. This may be done by flexing the region until the high modulus material work hardens and breaks. Alternatively, the hinge region may not need to be broken. The dimensions included in FIG. 7 are illustrative of the size of the various elements of the preferred haptic.

Figure 8A:
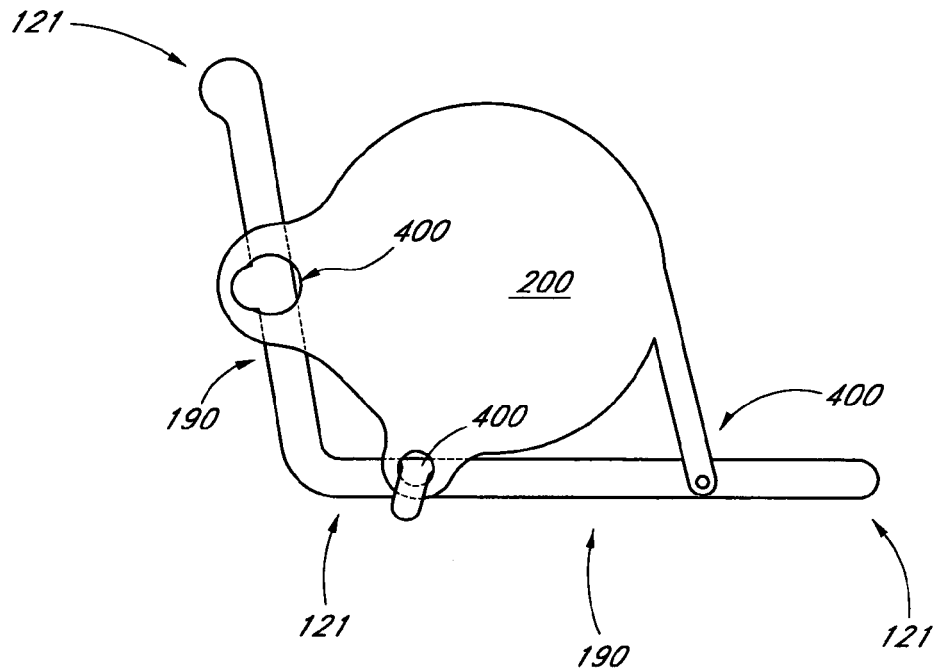
FIGS. 8A-H are plan views of alternative embodiments of the invention.
Figure 8B:
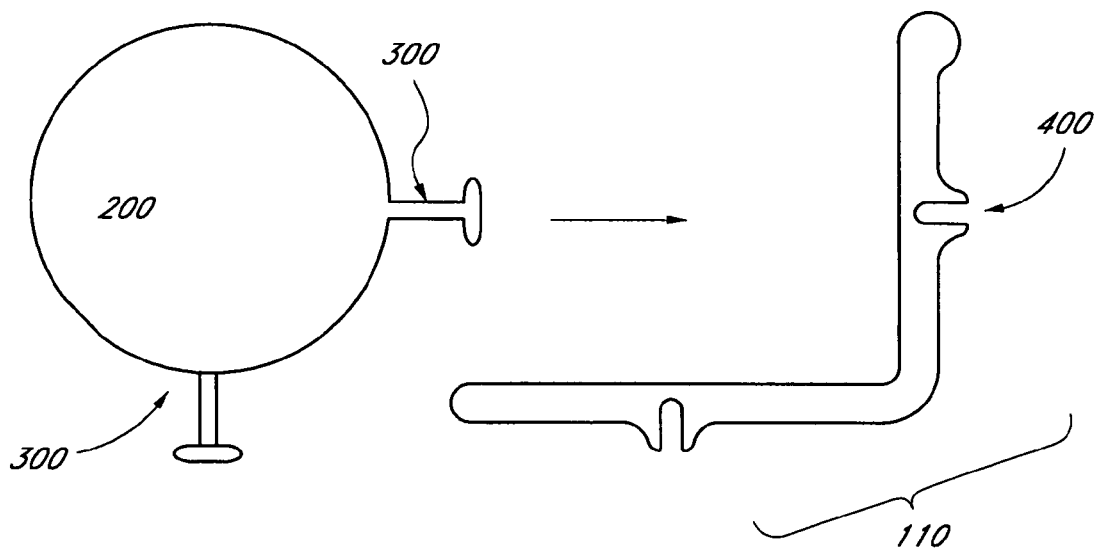
Figure 8C:
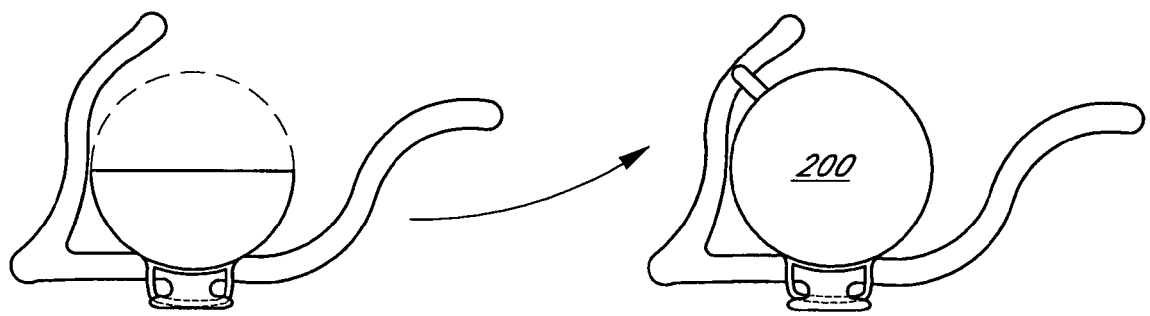
Figure 8D:
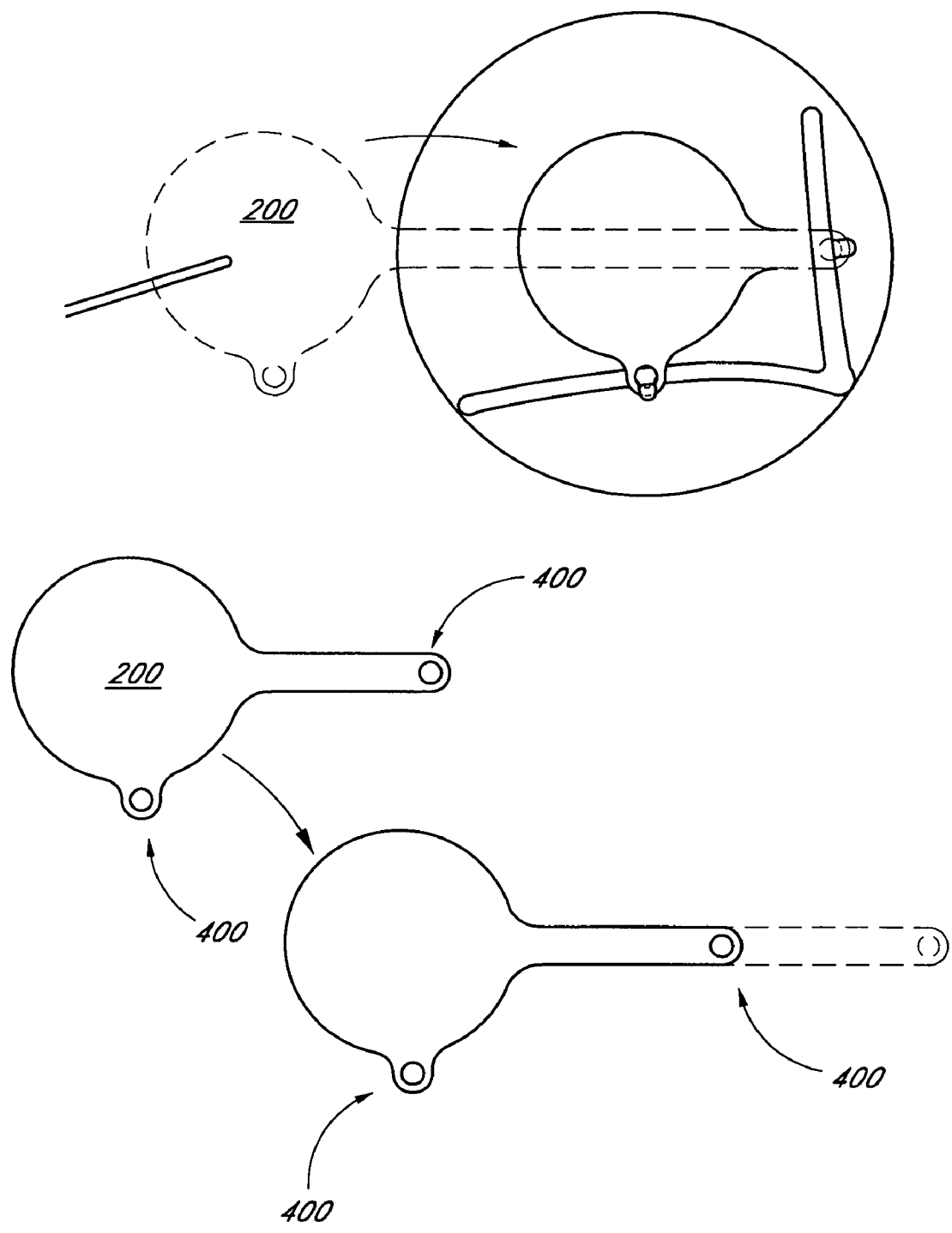
Figure 8E:
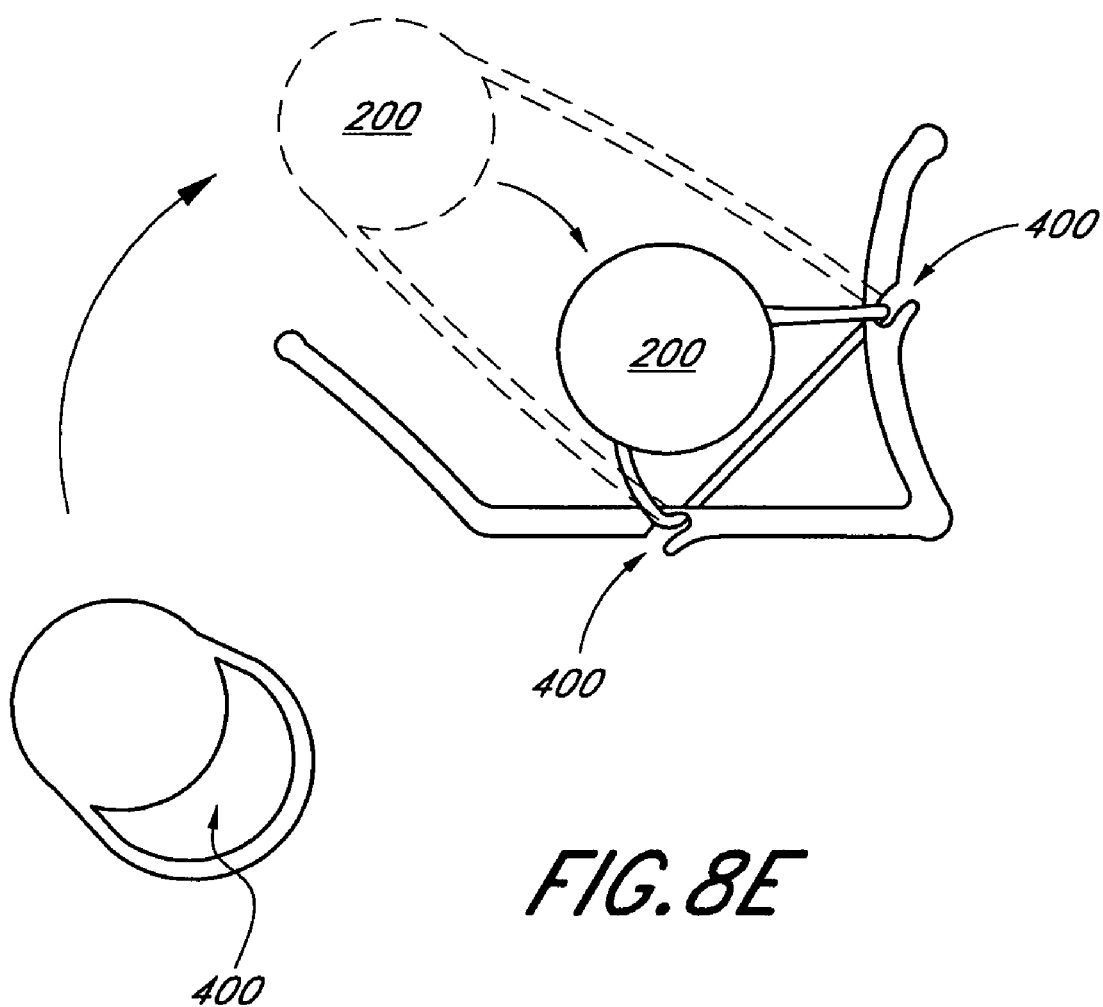
Figure 8F:
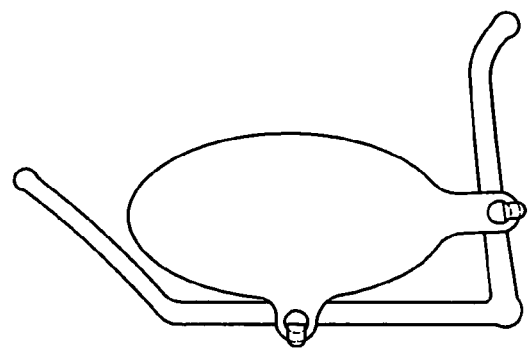

Alternative embodiments of the invention are shown in FIGS. 8A-H. In FIG. 8A an IOL is shown which possesses three attachments. The lens 200 possesses three eyelets 400 of various sizes and shapes. The angles of the eyelets 400 within the lens ($\alpha$, $\beta$, and $\phi$, $\sigma$ and $\theta$) can be the same or different. This provides for angular non-symmetry. FIG. 8B is an alternative which has the cleats 300 on the lens 200 and the slots, eyelets, apertures or notches 400 on the haptic 110. The lens is attached by pulling the ears of the cleat 300 through the slots 400. FIG. 8C is an alternative embodiment showing one long cleat 300 and one long slot 400. The lens may have one or more additional tabs for stability. In this embodiment, the lens 200 can be pre-attached and rolled for insertion with the haptic much like the haptic in FIGS. 5A-E, however steps F-H would differ in that the lens would simply "unroll" once the haptic is in the correct position in the eye. FIGS. 8D1 and 2 show an embodiment of the multi-part IOL in which the lens is attached with a very stretchable eyelet 400 at least one attachment site, such that the haptic can be inserted as in FIGS. 5A-E with the lens remaining outside of the incision. The eyelet 400 may elongate up to 300% its length (see FIG. 8D2). Then, as a last step, the lens is rolled or folded, inserted into the incision, and allowed to pull or snap back to its starting position on the haptic 110. As shown in FIG. 8D2, the lens 200 can also include a second eyelet 400 or tab which provides more stability to the lens 200 on the haptic 110. The eyelet 400 may alternatively have a sidways hole (see FIG. 8D2). FIG. 8E shows a further alternative embodiment in which the optic 200 has a single large eyelet 400 which forms a stretchable band and may be as wide as the lens. In this embodiment, the eyelet 400 can stretch away from the rigid frame during manipulation during implant of the IOL. Once it springs back into position, a slight outward tension holds the lens 200 flat. In this case the haptic 110 has two notches with which the eyelet 400 attaches at two separate points to hold the lens flat with a slight outward tension. Alternatively, IOL's are fabricated with only one eyelet. Since the weight of an optic in an aqueous solution, such as that in the eye, is significantly reduced in the aqueous of the eye, the buoyant effects produce a weight of only ¹/₁₀ of that in air. So the single eyelet serves more as a positional support then a weight support.

Figure 8G:
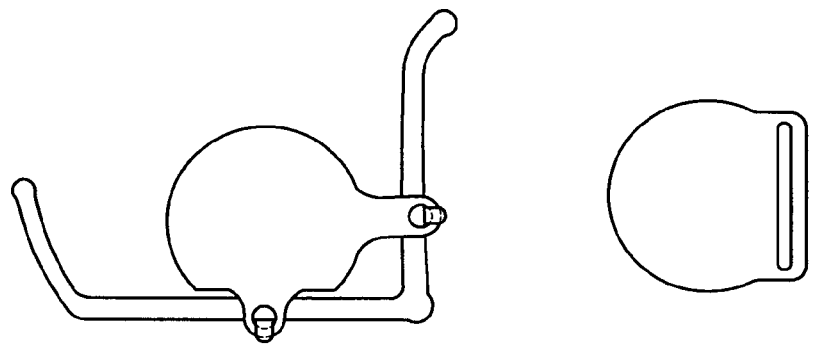
Figure 8H:
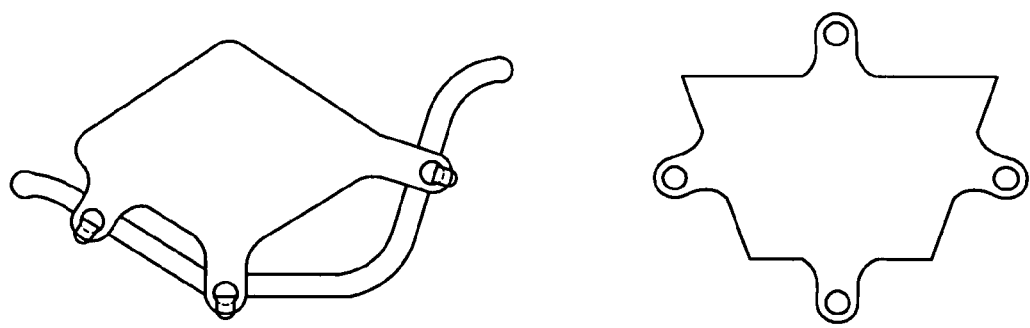

In most previous IOL's, the lenses have predominantly been round. However, it can be envisioned that the lens can be of many shapes. For example, in FIG. 8F, the lens is oval, which would advantageously make the IOL narrower. In FIG. 8G the lens is segmented or chopped at one side to reduce the overall width of the IOL. In FIG. 8H the optic has a parallelogram shape or even a trapezoid shape again allowing for a reduction in overall width. In this case the IOL may have up to four eyelets or even up to six.

Example 1

Insertion of the Two Part IOL into the Eye

A 2 mm incision is made near the limbus of the eye. Buffers are injected into the anterior chamber. The frame is inserted as shown in FIGS. 5A-H by a rotation action. The surgeon grasps the folded optic with the outside (distal) eyelet leading forward. The surgeon then pushes the lens through the incision and hooks the distal eyelet onto the distal cleat of the frame. Then, the surgeon slowly opens the forceps while maintaining slight tension. The lens is then grasped near or onto the closest eyelet (proximal) and pulls it over the closer cleat of the frame.

Therefore, the IOL of the present invention presents a number of advantages. It is inserted in two separate pieces significantly reducing the bulk so that the incision can be as narrow as 1 mm. It is lightweight and thin which reduces corneal chafing and pupilary block. In addition, because of the hinges and toes and arcuate shape, it is capable of being inserted and resting on the anterior chamber angle with a minimum of damage to the tissues as well as a minimum of discomfort to the patient. The fact that it is a plate haptic shape eliminates the problem of synechiae, and it can be used in a phakic or aphakic eye.

One advantage of the present invention is that because the lens is a multi-part assembly, the ideal properties of each part of the IOL can be retained. For example, the haptic is ideally more rigidly springy and can be constructed to fit into a very narrow incision without deformation. The lens, although it is between 4 mm and 7 mm, can be inserted into a narrow incision because it is constructed of a more pliable and soft material and can be folded, squeezed or rolled, more than it could be with the attached haptic, to be inserted into a considerably smaller incision. Therefore a multi-part IOL allows for insertion into a much narrower incision, than an assembled lens.

The lens can be implanted into the eye using a variety of surgical implant techniques known in the art. Although the preferred embodiment is that the lens be implanted into the anterior chamber, using the anterior chamber angles, it can be envisioned that the lens could also be implanted in the posterior chamber.

Additionally, any combination of the materials used will result in a lens that can be sterilized by a variety of standard methods such as ethylene oxide (ETO) or steam autoclaving at 250° F. or any other acceptable method and the lens will show long term biocompatablity and hydrolytic stability.

While this invention has been described with respect to various specific examples and embodiments, it is to be understood that the invention is not limited thereto and that it can be variously practiced within the scope of the following claims:

What is claimed is:

1. An attachment for a two-part IOL configured to be inserted through a small incision in an eye, said attachment comprising:
    a lens optic;
    a lens haptic configured to be inserted through the small incision in the eye without being folded, said lens haptic being more rigid than said lens optic;
    at least two cleats provided on said lens haptic; and
    at least two stretchable eyelets provided in said lens optic and configured to be stretched to firmly attach to respective said cleats provided on said lens haptic; wherein said lens haptic includes:
    a first rigid element;
    a second rigid element, said first and second rigid elements are separated from one another at a discontinuity; and
    a relatively less rigid element formed of a relatively lower modulus material than said first and second rigid elements, said relatively less rigid element bridging said discontinuity.

2. The attachment for a two-part IOL of claim 1, wherein said lens haptic includes at least one more cleat.

3. The attachment for a two-part IOL of claim 2, wherein said at least two cleats are positioned asymmetrical on said lens haptic.

4. The attachment for a two-part IOL of claim 1, wherein said lens haptic includes a hinge.

5. The attachment for a two-part IOL of claim 4, wherein said hinge comprises a toe region, a foot region, and a lower modulus material extended toward the foot region.

6. The attachment for a two-part IOL of claim 1, wherein said bridging allows for the second element to be rotated into the anterior chamber.

7. The attachment for a two-part IOL of claim 1, wherein said haptic is composed of a higher modulus material selected from the group consisting of: polyimide, polyetheretherketone, polycarbonate, polymethylpentene, polymethylmethyl, methacrylate, polypropylene, polyvinylidene fluoride, polysulfone, and polyether sulfone.

8. The attachment for a two-part IOL of claim 7, wherein said polyimide is KAPTON.

9. The attachment for a two-part IOL of claim 7, wherein said higher modulus material is polyphenylsulfone (PPSU).

10. The attachment for a two-part IOL of claim 7, wherein said higher modulus material has a modulus of about 100,000 to about 500,000 psi/inch.

11. The attachment for a two-part IOL of claim 10, wherein said higher modulus material has a modulus of about 340,000 psi/inch.

12. The attachment for a two-part IOL of claim 7, wherein said higher modulus material is less than or equal to about 0.01 inches thick.

13. The attachment for a two-part IOL of claim 1, wherein said lower modulus material is an elastomer selected from the group consisting of: silicones, urethane, or hydrophilic acrylics.

14. The attachment for a two-part IOL of claim 1, wherein said lower modulus material has a modulus of about 100 to about 1000 psi.

15. The attachment for a two-part IOL of claim 1, wherein said lower modulus material has a hardness of about 15 to 70 on the shore A scale.

16. The attachment for a two-part IOL of claim 1, wherein said higher modulus material has a hardness of 60 to 95 shore D.

17. The attachment for a two-part IOL of claim 1, wherein said lower modulus material is selected from the group consisting of: NUSIL MED 6600, 6604, 6607, 6400, and 6820.

18. The attachment for a two-part IOL of claim 1, wherein said optic is selected from the group consisting of a refractive lens, an interference lens, a toric lens, a multifocal lens, a positive lens, and a negative lens.

19. The attachment for a two-part IOL of claim 1, wherein a lower modulus material partially or completely covers said haptic.

20. The attachment for a two-part IOL of claim 1, wherein said lower modulus material is applied by surface treatment and molding.

21. The attachment for a two-part IOL of claim 20, wherein said surface treatment is a corona or plasma treatment.

22. The attachment for a two-part IOL of claim 20, wherein said molding is selected from the group consisting of dip molding, cast molding, and injection molding.

23. The attachment for a two-part IOL of claim 1, wherein said two part IOL is configured to pass completely through a 2.5 mm or less opening without folding the haptic.

24. The attachment for a two-part IOL of claim 1, wherein the haptic is generally "L" shaped.

25. The attachment for a two-part IOL of claim 1, wherein said eyelets are attached firmly, but moveably to allow for natural movement of the eye.

26. The attachment for a two-part IOL of claim 1, wherein when the eyelets are attached to the cleats, part of the eyelet passes beneath the plane of said lens optic.

27. An attachment for a two-part IOL configured to be inserted through a small incision in an eye, said attachment comprising:
  a lens optic;
  a lens haptic configured to be inserted through the small incision in the eye without folding said lens haptic, said lens haptic being more rigid than said lens optic;
  at least two cleats provided on said lens optic, said cleats extending generally in a plane of said lens optic; and
  at least two stretchable eyelets provided in said lens haptic and configured to be stretched to firmly attach to respective said cleats provided on said lens optic; wherein said lens haptic includes:
  a first rigid element;
  a second rigid element, said first and second rigid elements are separated from one another at a discontinuity; and
  a relatively less rigid element formed of a relatively lower modulus material than said first and second rigid elements, said relatively less rigid element bridging said discontinuity.

28. An attachment for a two-part IOL configured to be inserted through a small incision in an eye, said attachment comprising:
  a lens optic configured to be inserted through the small incision into the eye;
  a lens haptic configured to be inserted through the small incision into the eye without folding said lens haptic, said lens haptic being more rigid than said lens optic;
  at least two cleats provided on said lens optic, said cleats extending generally in a plane of said lens optic; and
  at least two stretchable eyelets provided in said lens haptic and configured to be stretched to firmly attach to respective said cleats provided on said lens optic,
  wherein said optic and said haptic are each configured to pass separately, completely through a small incision without folding the haptic, and wherein said cleats on the optic extend generally in the plane of the optic; wherein said lens haptic includes:
  a first rigid element;
  a second rigid element, said first and second rigid elements are separated from one another at a discontinuity; and
  a relatively less rigid element formed of a relatively lower modulus material than said first and second rigid elements, said relatively less rigid element bridging said discontinuity.

29. An attachment for a two-part IOL configured to be inserted through a small incision in an eye, said attachment comprising:
  a lens optic configured to be independently inserted through the small incision in the eye;
  a lens haptic configured to be independently inserted through the small incision in the eye without folding said lens haptic;
  at least two cleats provided on said lens haptic; and
  at least two stretchable eyelets provided in said lens optic and configured to be stretched to firmly attach to respective said cleats provided on said lens haptic; wherein said lens haptic includes:
  a first rigid element;
  a second rigid element, said first and second rigid elements are separated from one another at a discontinuity; and
  a relatively less rigid element formed of a relatively lower modulus material than said first and second rigid elements, said relatively less rigid element bridging said discontinuity.

* * * * *